United States Patent
Wang et al.

(10) Patent No.: US 10,430,943 B2
(45) Date of Patent: Oct. 1, 2019

(54) AUTOMATED NUCLEI AREA/NUMBER ESTIMATION FOR IHC IMAGE ANALYSIS

(71) Applicant: SONY CORPORATION, Tokyo (JP)

(72) Inventors: Su Wang, San Jose, CA (US); Xun Xu, Palo Alto, CA (US); Akira Nakamura, San Jose, CA (US)

(73) Assignee: Sony Corporation, Tokyo (JP)

( * ) Notice: Subject to any disclaimer, the term of this patent is extended or adjusted under 35 U.S.C. 154(b) by 117 days.

(21) Appl. No.: 15/288,776

(22) Filed: Oct. 7, 2016

(65) Prior Publication Data

US 2018/0101949 A1  Apr. 12, 2018

(51) Int. Cl.
 *G06K 9/00* (2006.01)
 *G06T 7/00* (2017.01)
 (Continued)

(52) U.S. Cl.
 CPC ....... *G06T 7/0012* (2013.01); *G01N 15/0205* (2013.01); *G01N 33/57496* (2013.01);
 (Continued)

(58) Field of Classification Search
 CPC ......... G06K 2009/366; G06K 9/00127; G06K 9/0014; G06K 9/00147; G06K 9/00523; G06K 9/0053; G06K 9/00536; G06K 9/3233; G06K 9/3241; G06K 9/34; G06K 9/342; G06K 9/36; G06K 9/38; G06K 9/40; G06K 9/44; G06K 9/46; G06K 9/4638; G06K 9/4652; G06K 9/62; G06K 9/6201; G06K 9/6209; G06K 9/621; G06K 9/6215; G06K 9/6217; G06K 9/6218; G06K 9/6231; G06K 9/6253; G06K 9/6254;
 (Continued)

(56) References Cited

U.S. PATENT DOCUMENTS

| | | | | |
|---|---|---|---|---|
| 8,116,551 | B2 * | 2/2012 | Gallagher | ............ G06K 9/0014 382/128 |
| 8,831,327 | B2 * | 9/2014 | Santamaria-Pang | ... G16B 40/00 382/133 |

(Continued)

FOREIGN PATENT DOCUMENTS

| | | |
|---|---|---|
| EP | 1380005 A1 | 1/2004 |
| WO | 02097714 A1 | 12/2002 |
| WO | 2016120442 A1 | 8/2016 |

OTHER PUBLICATIONS

Varun Oswal, Ashwin Belle, Robert Diegelmann, and Kayvan Najarian, "An Entropy-Based Automated Cell Nuclei Segmentation and Quantification: Application in Analysis of Wound Healing Process", Computational and Mathematical Methods in Medicine, Mar. 2013, pp. 1-10.*

(Continued)

Primary Examiner — Eric Rush
(74) Attorney, Agent, or Firm — Haverstock & Owens LLP

(57) ABSTRACT

Automated nuclei area/number estimation utilizes a two-stage estimation framework-area estimation first followed by number estimation. After determining area information, each local patch's shape features are able to be extracted to define a local voting rule. The resulting voting score determines the strength of each local voting peak. The number of voting peaks is exactly the number of nuclei.

20 Claims, 2 Drawing Sheets

(51) Int. Cl.
*G06K 9/34* (2006.01)
*G01N 15/02* (2006.01)
*G06K 9/46* (2006.01)
*G01N 33/574* (2006.01)
*G06T 7/11* (2017.01)
*G06T 7/136* (2017.01)

(52) U.S. Cl.
CPC ....... *G06K 9/0014* (2013.01); *G06K 9/00127* (2013.01); *G06K 9/00147* (2013.01); *G06K 9/342* (2013.01); *G06K 9/4604* (2013.01); *G06K 9/4638* (2013.01); *G06T 7/11* (2017.01); *G06T 7/136* (2017.01); *G06T 2207/10024* (2013.01); *G06T 2207/10056* (2013.01); *G06T 2207/20081* (2013.01); *G06T 2207/20104* (2013.01); *G06T 2207/30024* (2013.01)

(58) Field of Classification Search
CPC .. G06K 9/6256; G06K 9/6267; G06K 9/4604; G06T 7/0012; G06T 7/10; G06T 7/136; G06T 7/194; G06T 7/60; G06T 7/62; G06T 7/64; G06T 2207/20004; G06T 2207/20012; G06T 2207/20081; G06T 2207/20084; G06T 2207/20104; G06T 2207/20112; G06T 2207/30004; G06T 2207/30024; G06T 2207/30242; G06T 7/11; G06T 2207/10024; G06T 2207/10056; G01N 15/02; G01N 15/0205; G01N 15/1463; G01N 15/1468; G01N 15/1475; G01N 2015/1465; G01N 2015/1472; G01N 2015/1486; G01N 2015/1493; G01N 2015/1497; G01N 33/48; G01N 33/483; G01N 33/57496
USPC ....... 382/100, 128, 129, 133, 134, 155, 156, 382/159, 160, 162, 164, 165, 171, 173, 382/181, 190, 199, 203, 224, 225, 254, 382/260, 261, 270–275, 286; 435/287.1, 435/288.1; 702/19–29
See application file for complete search history.

(56) References Cited

U.S. PATENT DOCUMENTS

| | | | | |
|---|---|---|---|---|
| 9,014,444 | B2* | 4/2015 | Liu | G06K 9/0014 |
| | | | | 382/128 |
| 9,558,393 | B2* | 1/2017 | Ichitani | G06T 7/0012 |
| 2002/0186875 | A1* | 12/2002 | Burmer | G06K 9/00127 |
| | | | | 382/133 |
| 2005/0136549 | A1* | 6/2005 | Gholap | G06K 9/0014 |
| | | | | 436/501 |
| 2005/0272073 | A1* | 12/2005 | Vaisberg | G01N 33/5005 |
| | | | | 435/6.13 |
| 2006/0014238 | A1 | 1/2006 | Gholap et al. | |
| 2013/0121565 | A1* | 5/2013 | Wang | G06K 9/6215 |
| | | | | 382/159 |
| 2013/0230230 | A1* | 9/2013 | Ajemba | G06T 7/0012 |
| | | | | 382/133 |
| 2013/0301898 | A1* | 11/2013 | Jain | G06T 7/0012 |
| | | | | 382/133 |
| 2013/0315466 | A1* | 11/2013 | Drell | G06K 9/00127 |
| | | | | 382/133 |
| 2014/0377753 | A1* | 12/2014 | Bamford | G06T 7/0012 |
| | | | | 435/6.11 |
| 2015/0169985 | A1* | 6/2015 | Burger | G06K 9/4638 |
| | | | | 382/133 |
| 2017/0169567 | A1* | 6/2017 | Chefd'hotel | G06K 9/00127 |
| 2017/0309021 | A1* | 10/2017 | Barnes | G06T 7/0012 |
| 2017/0337695 | A1* | 11/2017 | Sarkar | G06T 7/194 |
| 2018/0012355 | A1* | 1/2018 | Sarkar | G06T 7/0012 |
| 2018/0040120 | A1* | 2/2018 | Faelan | G06K 9/00147 |
| 2018/0260609 | A1* | 9/2018 | Georgescu | G06K 9/00127 |

OTHER PUBLICATIONS

Oswal, Varun et al., "An Entropy-Based Automated Cell Nuclei Segmentation and Quantification : Application in Analysis of Wound Healing Process", Hindawi Publishing Corporation, vol. 13, Article ID 592790, pp. 10, 2013.

International Search Report and Written Opinion of the International Searching Authority, dated Nov. 14, 2017, from PCT Application No. PCT/US2017/047004.

* cited by examiner

AUTOMATED NUCLEI AREA/NUMBER ESTIMATION FOR IHC IMAGE ANALYSIS

FIELD OF THE INVENTION

The present invention relates to the field of imaging. More specifically, the present invention relates to medical imaging.

BACKGROUND OF THE INVENTION

Immunohistochemistry (IHC) refers to the process of detecting proteins in cells of a tissue section. IHC staining is widely used in the diagnosis of abnormal cells such as those found in cancerous tumors. Common practice in pathology laboratories is to score IHC-stained images. By indicating a tumor is negative or positive, the percentage of positively stained tumor cell nuclei is able to be reported, which is able to assist pathologists for the final scoring purpose.

Some research has been done for the percentage estimation of positively stained tumor cell nuclei. The goal is achieved by using a color de-convolution algorithm for separating the staining components (diaminobenzidine and hematoxylin) and adaptive thresholding for nuclear area segmentation. The quantitative results are calibrated using cell counts defined visually as the gold standard.

Most of the nuclei area estimation algorithms require a user to manually specify a cut-off threshold value for defining positive/negative. Although this type of user interaction is allowed, it is able to be improved.

However, most of the existing research work is performing nuclei area estimation, which is fast in speed but does not provide nuclei number estimation. According to pathologists, number information is a plus and is able to be provide extra hints when scoring IHC-stained images.

Nuclei's shapes and image intensities vary significantly. Touching cases (e.g., when nuclei are connected with each other) makes the number estimation even more challenging. Under-estimation and over-estimation are two major issues when developing automated nuclei number estimation.

SUMMARY OF THE INVENTION

Automated nuclei area/number estimation utilizes a two-stage estimation framework-area estimation first followed by number estimation. After determining area information, each local patch's shape features are able to be extracted to define a local voting rule. The resulting voting score determines the strength of each local voting peak. The number of voting peaks is exactly the number of nuclei.

In one aspect, a method programmed in a non-transitory memory of a device comprises performing nuclei area estimation and performing nuclei number estimation for detecting abnormal cells. Performing nuclei area estimation comprises: receiving a color image. Performing nuclei area estimation comprises: utilizing stain separation to separate two dominating color components, a first color corresponding to positive stains and a second color corresponding to negative stains. Performing nuclei area estimation comprises: adaptive thresholding based on each color channel. Performing nuclei area estimation comprises: wherein a small region of interest is selected for model training. Performing nuclei area estimation comprises: utilizing a user-selected region of interest as training data to enhance the image quality of stain separation via model training and selection. Performing nuclei area estimation comprises: applying a Gaussian Mixture Model (GMM) to parameterize user-selected data distribution, and clustering is performed for a remaining area. Performing nuclei area estimation comprises: selecting a class with the highest mean stain separation value. Performing nuclei area estimation comprises: hard thresholds are applied to adaptively-enhanced stain separation images to determine a nuclear area. The thresholds are user-specified values. The thresholds are searched optimum values. Performing nuclei number estimation comprises: after receiving segmented patches, connected component analysis is applied to analyze each local patch's shape which define rules for local center voting. Performing nuclei number estimation comprises: voting on the center of each nuclear area, such that the higher the voting score, the more likely to be a real nuclear center. Performing nuclei number estimation comprises: filtering peaks caused by artifacts using local shape-determined rules. Performing nuclei number estimation comprises: determining the number nuclei based on the number of voting peaks, wherein the number of nuclei is the same as the number of nuclei. The device comprises a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player, a high definition disc writer/player, an ultra high definition disc writer/player), a television, a home entertainment system, or a smart watch.

In another aspect, a method programmed in a non-transitory memory of a device comprises performing nuclei area estimation including: receiving a color image, utilizing stain separation to separate two dominating color components of the color image, a first color corresponding to positive stains and a second color corresponding to negative stains, performing adaptive thresholding based on each color channel, selecting a small region of interest for model training, utilizing a user-selected region of interest as training data to enhance the image quality of stain separation via the model training and selection, applying a Gaussian Mixture Model (GMM) to parameterize user-selected data distribution and performing clustering for a remaining area, selecting a class with the highest mean stain separation value, applying hard thresholds to the adaptively-enhanced stain separation image to determine a nuclear area and performing nuclei number estimation for detecting abnormal cells including: after receiving segmented patches, connected component analysis is applied to analyze each local patch's shape which define rules for local center voting, voting on the center of each nuclear area, such that the higher the voting score, the more likely to be a real nuclear center, filtering peaks caused by artifacts using local shape-determined rules and determining the number nuclei based on the number of voting peaks, wherein the number of nuclei is the same as the number of nuclei. The hard thresholds are user-specified values. The hard thresholds are searched optimum values. The device comprises a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player, a high definition disc writer/player, an ultra high definition disc writer/player), a television, a home entertainment system, or a smart watch.

In another aspect, an apparatus comprises a non-transitory memory for storing an application, the application for: performing nuclei area estimation including: receiving a color image, utilizing stain separation to separate two dominating color components of the color image, a first color corresponding to positive stains and a second color corresponding to negative stains, performing adaptive thresholding based on each color channel, selecting a small region of interest for model training, utilizing a user-selected region of interest as training data to enhance the image quality of stain separation via the model training and selection, applying a Gaussian Mixture Model (GMM) to parameterize user-selected data distribution and performing clustering for a remaining area, selecting a class with the highest mean stain separation value and applying hard thresholds to the adaptively-enhanced stain separation image to determine a nuclear area and performing nuclei number estimation for detecting abnormal cells including: after receiving segmented patches, connected component analysis is applied to analyze each local patch's shape which define rules for local center voting, voting on the center of each nuclear area, such that the higher the voting score, the more likely to be a real nuclear center, filtering peaks caused by artifacts using local shape-determined rules and determining the number nuclei based on the number of voting peaks, wherein the number of nuclei is the same as the number of nuclei and a processing component coupled to the memory, the processing component configured for processing the application. The hard thresholds are user-specified values. The hard thresholds are searched optimum values.

In yet another aspect, an apparatus comprises a non-transitory memory for storing an application, the application for: performing nuclei area estimation and performing nuclei number estimation for detecting abnormal cells and a processing component coupled to the memory, the processing component configured for processing the application. Performing nuclei area estimation includes: receiving a color image, utilizing stain separation to separate two dominating color components of the color image, a first color corresponding to positive stains and a second color corresponding to negative stains, performing adaptive thresholding based on each color channel, selecting a small region of interest for model training, utilizing a user-selected region of interest as training data to enhance the image quality of stain separation via the model training and selection, applying a Gaussian Mixture Model (GMM) to parameterize user-selected data distribution and performing clustering for a remaining area, selecting a class with the highest mean stain separation value and applying hard thresholds to the adaptively-enhanced stain separation image to determine a nuclear area. Performing nuclei number estimation for detecting abnormal cells further includes: after receiving segmented patches, connected component analysis is applied to analyze each local patch's shape which define rules for local center voting, voting on the center of each nuclear area, such that the higher the voting score, the more likely to be a real nuclear center, filtering peaks caused by artifacts using local shape-determined rules and determining the number nuclei based on the number of voting peaks, wherein the number of nuclei is the same as the number of nuclei.

DETAILED DESCRIPTION OF THE PREFERRED EMBODIMENT

An automated nuclei area and number estimation method and system enable improved Immunohistochemistry (IHC) image analysis.

The automated nuclei area and number estimation system uses a two-stage estimation framework: nuclear area estimation (e.g., number of nuclear pixels) followed by nuclear number estimation. Nuclear area is estimated from a binarized patch or patches, and these segmented patches provide local shape features which are able to facilitate number estimation.

To better distinguish a nuclear target and artifacts, the image quality of stain separation is enhanced by performing adaptive clustering based on a user-selected Region of Interest (ROI) via model training/selection.

To estimate nuclei area, stain separation is applied to separate two dominating color components, one corresponding to positive stains and the other one corresponding to negative stains. Area estimation is performed based on each color channel by adaptive thresholding. The system intelligently utilizes a user-selected ROI as the training data to enhance the image quality of stain separation via model training and selection. Regarding model training, a Gaussian Mixture Model (GMM) is applied to parameterize the user-selected region of interest data distribution, and clustering (model selection) is performed for the remaining area not a part of the user-selected region of interest. To determine a nuclear area, adaptively-enhanced stain separation images are hard thresholded, either by user-specified values or searched optimum values.

Nuclei number estimation is based on the aforementioned nuclear area estimation. More specially, after determining segmented patches, connected component analysis (CCA) is applied to analyze each local patch's shape. These shape features help define the rules for local center voting. Local center voting is an important algorithm to determine nuclei numbers. This gradient-based algorithm votes the center of each nuclear, such that the higher the voting score, the more likely to be a real nuclear center. And those local shape-determined rules help to filter out those peaks caused by artifacts. Finally, the number of voting peaks is exactly the number of nuclei. The following shape features are utilized (although others are able to be used):

Convex ratio

Major axis length/minor axis length

Figure 1:
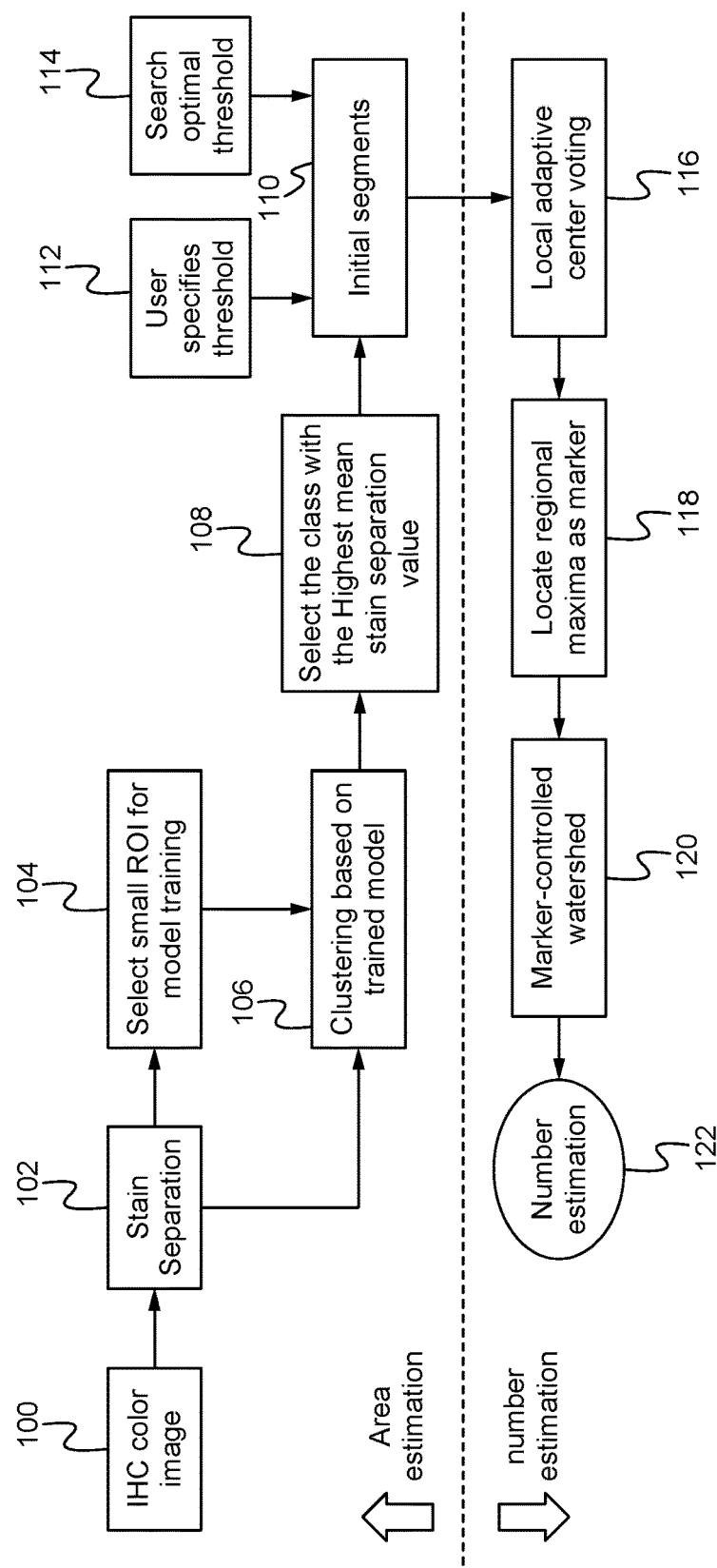
FIG. 1 illustrates a flowchart of a method of automated nuclei area and number estimation according to some embodiments.

FIG. 1 illustrates a flowchart of a method of automated nuclei area and number estimation according to some embodiments. In the step 100, an IHC color image is acquired. For example, the IHC color image is retrieved from a data storage. In the step 102, stain separation is utilized to separate two dominating color components, one corresponding to positive stains and the other one corresponding to negative stains. Stain separation is able to be performed in any manner; for example, automatically detecting two different colors. Area estimation is performed based on each color channel by adaptive thresholding such that the threshold changes dynamically over the image. In the step 104, a small ROI (e.g., less than a specified percent of an image such as 2%) is selected for model training. The system intelligently utilizes a user-selected (or computer-selected) ROI as the training data to enhance the image quality of stain separation via model training and selection. Regarding model training, a Gaussian Mixture Model (GMM) is applied to parameterize user-selected data distribution, and clustering (model selection) is performed for the remaining area, in the step 106. The clustering generates clusters or classes based on mean stain separation values. In the step 108, the class with the highest mean stain separation value is selected. In the step 110, to determine the nuclear area, adaptively-enhanced stain separation images are hard thresholded, either by user-specified values, in the step 112, or searched optimum values, in the step 114. For example, a specified threshold is utilized to estimate the nuclear area.

Nuclei number estimation is based on the aforementioned nuclear area estimation. More specially, after determining segmented patches, connected component analysis (CCA) is applied to analyze each local patch's shape. These shape features help define the rules for local center voting, in the step 116. Local center voting is an important algorithm to determine nuclei numbers. Local center voting is a gradient-based algorithm which votes on the center of each nuclear area, such that the higher the voting score, the more likely to be a real nuclear center, in the step 118. The local shape-determined rules help to filter out the peaks caused by artifacts, in the step 120. Finally, the number of voting peaks is exactly the number of nuclei, in the step 122.

Figure 2:
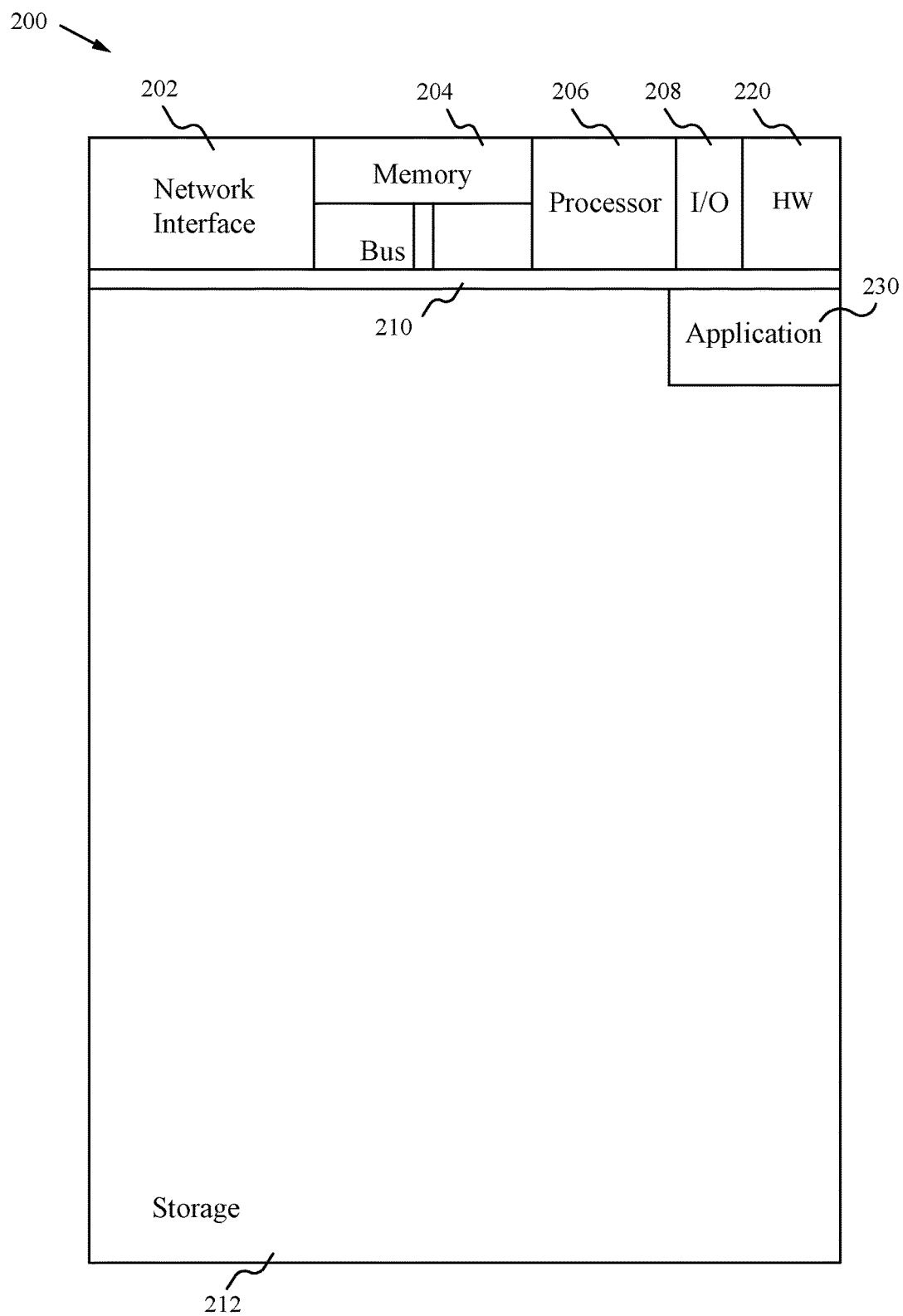
FIG. 2 illustrates a block diagram of an exemplary computing device configured to implement the automated nuclei area/number estimation method according to some embodiments.

FIG. 2 illustrates a block diagram of an exemplary computing device configured to implement the automated nuclei area/number estimation method according to some embodiments. The computing device 200 is able to be used to acquire, store, compute, process, communicate and/or display information such as images and videos. In general, a hardware structure suitable for implementing the computing device 200 includes a network interface 202, a memory 204, a processor 206, I/O device(s) 208, a bus 210 and a storage device 212. The choice of processor is not critical as long as a suitable processor with sufficient speed is chosen. The memory 204 is able to be any conventional computer memory known in the art. The storage device 212 is able to include a hard drive, CDROM, CDRW, DVD, DVDRW, High Definition disc/drive, ultra-HD drive, flash memory card or any other storage device. The computing device 200 is able to include one or more network interfaces 202. An example of a network interface includes a network card connected to an Ethernet or other type of LAN. The I/O device(s) 208 are able to include one or more of the following: keyboard, mouse, monitor, screen, printer, modem, touchscreen, button interface and other devices. Automated nuclei area/number estimation application(s) 230 used to perform the automated nuclei area/number estimation method are likely to be stored in the storage device 212 and memory 204 and processed as applications are typically processed. More or fewer components shown in FIG. 2 are able to be included in the computing device 200. In some embodiments, automated nuclei area/number estimation hardware 220 is included. Although the computing device 200 in FIG. 2 includes applications 230 and hardware 220 for the automated nuclei area/number estimation method, the automated nuclei area/number estimation method is able to be implemented on a computing device in hardware, firmware, software or any combination thereof. For example, in some embodiments, the automated nuclei area/number estimation applications 230 are programmed in a memory and executed using a processor. In another example, in some embodiments, the automated nuclei area/number estimation hardware 220 is programmed hardware logic including gates specifically designed to implement the automated nuclei area/number estimation method.

In some embodiments, the automated nuclei area/number estimation application(s) 230 include several applications and/or modules. In some embodiments, modules include one or more sub-modules as well. In some embodiments, fewer or additional modules are able to be included.

Examples of suitable computing devices include a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player (e.g., DVD writer/player, high definition disc writer/player, ultra high definition disc writer/player), a television, a home entertainment system, smart jewelry (e.g., smart watch) or any other suitable computing device.

To utilize automated nuclei area/number estimation, an IHC color image is analyzed using automated nuclei area/number estimation. Based on the results of automated nuclei area/number estimation, a pathologist is able to further determine if a tumor is cancerous or not.

In operation, automated nuclei area/number estimation provides a benefit based on its two-stage estimation framework-area estimation first followed by number estimation. After determining area information, each local patch's shape features are able to be extracted to define a local voting rule. The resulting voting score determines the strength of each local voting peak. The number of voting peaks is exactly the number of nuclei.

Some Embodiments of Automated Nuclei Area/Number Estimation for IHC Image Analysis 1. A method programmed in a non-transitory memory of a device comprising:
   a. performing nuclei area estimation; and
   b. performing nuclei number estimation for detecting abnormal cells.
2. The method of clause 1 wherein performing nuclei area estimation comprises: receiving a color image.
3. The method of clause 2 wherein performing nuclei area estimation comprises: utilizing stain separation to separate two dominating color components, a first color corresponding to positive stains and a second color corresponding to negative stains.
4. The method of clause 3 wherein performing nuclei area estimation comprises: adaptive thresholding based on each color channel.
5. The method of clause 4 wherein performing nuclei area estimation comprises: wherein a small region of interest is selected for model training.
6. The method of clause 5 wherein performing nuclei area estimation comprises: utilizing a user-selected region of interest as training data to enhance the image quality of stain separation via model training and selection.
7. The method of clause 6 wherein performing nuclei area estimation comprises: applying a Gaussian Mixture Model (GMM) to parameterize user-selected data distribution, and clustering is performed for a remaining area.
8. The method of clause 7 wherein performing nuclei area estimation comprises: selecting a class with the highest mean stain separation value.
9. The method of clause 8 wherein performing nuclei area estimation comprises: hard thresholds are applied to adaptively-enhanced stain separation images to determine a nuclear area.

10. The method of clause 9 wherein the thresholds are user-specified values.
11. The method of clause 9 wherein the thresholds are searched optimum values.
12. The method of clause 1 wherein performing nuclei number estimation comprises: after receiving segmented patches, connected component analysis is applied to analyze each local patch's shape which define rules for local center voting.
13. The method of clause 12 wherein performing nuclei number estimation comprises: voting on the center of each nuclear area, such that the higher the voting score, the more likely to be a real nuclear center.
14. The method of clause 13 wherein performing nuclei number estimation comprises: filtering peaks caused by artifacts using local shape-determined rules.
15. The method of clause 14 wherein performing nuclei number estimation comprises: determining the number nuclei based on the number of voting peaks, wherein the number of nuclei is the same as the number of nuclei.
16. The method of clause 1 wherein the device comprises a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player, a high definition disc writer/player, an ultra high definition disc writer/player), a television, a home entertainment system, or a smart watch.
17. A method programmed in a non-transitory memory of a device comprising:
    a. performing nuclei area estimation including:
        i. receiving a color image;
        ii. utilizing stain separation to separate two dominating color components of the color image, a first color corresponding to positive stains and a second color corresponding to negative stains;
        iii. performing adaptive thresholding based on each color channel;
        iv. selecting a small region of interest for model training;
        v. utilizing a user-selected region of interest as training data to enhance the image quality of stain separation via the model training and selection;
        vi. applying a Gaussian Mixture Model (GMM) to parameterize user-selected data distribution and performing clustering for a remaining area;
        vii. selecting a class with the highest mean stain separation value;
        viii. applying hard thresholds to the adaptively-enhanced stain separation image to determine a nuclear area; and
    b. performing nuclei number estimation for detecting abnormal cells including:
        i. after receiving segmented patches, connected component analysis is applied to analyze each local patch's shape which define rules for local center voting;
        ii. voting on the center of each nuclear area, such that the higher the voting score, the more likely to be a real nuclear center;
        iii. filtering peaks caused by artifacts using local shape-determined rules; and
        iv. determining the number nuclei based on the number of voting peaks, wherein the number of nuclei is the same as the number of nuclei.
18. The method of clause 17 wherein the hard thresholds are user-specified values.
19. The method of clause 17 wherein the hard thresholds are searched optimum values.
20. The method of clause 17 wherein the device comprises a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player, a high definition disc writer/player, an ultra high definition disc writer/player), a television, a home entertainment system, or a smart watch.
21. An apparatus comprising:
    a. a non-transitory memory for storing an application, the application for:
        i. performing nuclei area estimation including:
            (1) receiving a color image;
            (2) utilizing stain separation to separate two dominating color components of the color image, a first color corresponding to positive stains and a second color corresponding to negative stains;
            (3) performing adaptive thresholding based on each color channel;
            (4) selecting a small region of interest for model training;
            (5) utilizing a user-selected region of interest as training data to enhance the image quality of stain separation via the model training and selection;
            (6) applying a Gaussian Mixture Model (GMM) to parameterize user-selected data distribution and performing clustering for a remaining area;
            (7) selecting a class with the highest mean stain separation value; and
            (8) applying hard thresholds to the adaptively-enhanced stain separation image to determine a nuclear area; and
        ii. performing nuclei number estimation for detecting abnormal cells including:
            (1) after receiving segmented patches, connected component analysis is applied to analyze each local patch's shape which define rules for local center voting;
            (2) voting on the center of each nuclear area, such that the higher the voting score, the more likely to be a real nuclear center;
            (3) filtering peaks caused by artifacts using local shape-determined rules; and
            (4) determining the number nuclei based on the number of voting peaks, wherein the number of nuclei is the same as the number of nuclei; and
    b. a processing component coupled to the memory, the processing component configured for processing the application.
22. The apparatus of clause 21 wherein the hard thresholds are user-specified values.
23. The apparatus of clause 21 wherein the hard thresholds are searched optimum values.
24. An apparatus comprising:
    a. a non-transitory memory for storing an application, the application for:
        i. performing nuclei area estimation; and ii. performing nuclei number estimation for detecting abnormal cells; and
b. a processing component coupled to the memory, the processing component configured for processing the application.
25. The apparatus of clause 24 wherein performing nuclei area estimation includes:
(1) receiving a color image;
(2) utilizing stain separation to separate two dominating color components of the color image, a first color corresponding to positive stains and a second color corresponding to negative stains;
(3) performing adaptive thresholding based on each color channel;
(4) selecting a small region of interest for model training;
(5) utilizing a user-selected region of interest as training data to enhance the image quality of stain separation via the model training and selection;
(6) applying a Gaussian Mixture Model (GMM) to parameterize user-selected data distribution and performing clustering for a remaining area;
(7) selecting a class with the highest mean stain separation value; and
(8) applying hard thresholds to the adaptively-enhanced stain separation image to determine a nuclear area.
26. The apparatus of clause 24, wherein performing nuclei number estimation for detecting abnormal cells further includes:
(1) after receiving segmented patches, connected component analysis is applied to analyze each local patch's shape which define rules for local center voting;
(2) voting on the center of each nuclear area, such that the higher the voting score, the more likely to be a real nuclear center;
(3) filtering peaks caused by artifacts using local shape-determined rules; and
(4) determining the number nuclei based on the number of voting peaks, wherein the number of nuclei is the same as the number of nuclei.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:
1. A method programmed in a non-transitory memory of a device comprising:
performing nuclei area estimation with the device, the estimation comprising:
receiving a color image;
utilizing stain separation to separate two dominating color components, a first color corresponding to positive stains and a second color corresponding to negative stains;
identifying a user-selected region of interest of the color image; and
applying a Gaussian Mixture Model (GMM) to parameterize the user-selected region of interest's data distribution, and performing clustering for a remaining area of the color image that is not a part of the user-selected region of interest; and
performing nuclei number estimation for detecting abnormal cells with the device,
the nuclei number estimation comprising:
after receiving segmented patches, applying connected component analysis to analyze each local patch's shape; and
voting on the center of each nuclear area, such that the higher a voting score, the more likely to be a real nuclear center.
2. The method of claim 1 wherein performing nuclei area estimation comprises: adaptive thresholding based on each color channel.
3. The method of claim 2 wherein performing nuclei area estimation comprises: wherein a small region of interest is selected for model training.
4. The method of claim 3 wherein performing nuclei area estimation comprises: utilizing the user-selected region of interest as training data.
5. The method of claim 3 wherein performing nuclei area estimation comprises: hard thresholds are applied to adaptively-enhanced stain separation images to determine a nuclear area.
6. The method of claim 5 wherein the hard thresholds are user-specified values.
7. The method of claim 5 wherein the hard thresholds are searched optimum values.
8. The method of claim 1 wherein performing nuclei number estimation comprises: filtering peaks caused by artifacts based on a local patch's shape.
9. The method of claim 8 wherein performing nuclei number estimation comprises: determining the number nuclei based on a number of voting peaks, wherein the number of nuclei is the same as the number of voting peaks.
10. The method of claim 1 wherein the device comprises a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player, a high definition disc writer/player, an ultra high definition disc writer/player), a television, a home entertainment system, or a smart watch.
11. A method programmed in a non-transitory memory of a device comprising:
performing nuclei area estimation including:
receiving a color image;
utilizing stain separation to separate two dominating color components of the color image, a first color corresponding to positive stains and a second color corresponding to negative stains;
performing adaptive thresholding based on each color channel;
selecting a small region of interest for model training;
utilizing a user-selected region of interest as training data;
applying a Gaussian Mixture Model (GMM) to parameterize the user-selected region of interest's data distribution, and performing clustering for a remaining area of the color image that is not a part of the user-selected region of interest;
applying hard thresholds to an adaptively-enhanced stain separation image to determine a nuclear area; and
performing nuclei number estimation for detecting abnormal cells including:

after receiving segmented patches, applying connected component analysis to analyze each local patch's shape;
voting on the center of each nuclear area, such that the higher a voting score, the more likely to be a real nuclear center;
filtering peaks caused by artifacts based on a local patch's shape; and
determining the number nuclei based on a number of voting peaks, wherein the number of nuclei is the same as the number of voting peaks.

12. The method of claim 11 wherein the hard thresholds are user-specified values.

13. The method of claim 11 wherein the hard thresholds are searched optimum values.

14. The method of claim 11 wherein the device comprises a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player, a high definition disc writer/player, an ultra high definition disc writer/player), a television, a home entertainment system, or a smart watch.

15. An apparatus comprising:
a non-transitory memory for storing an application, the application for:
performing nuclei area estimation including:
receiving a color image;
utilizing stain separation to separate two dominating color components of the color image, a first color corresponding to positive stains and a second color corresponding to negative stains;
performing adaptive thresholding based on each color channel;
selecting a small region of interest for model training;
utilizing a user-selected region of interest as training data;
applying a Gaussian Mixture Model (GMM) to parameterize the user-selected region of interest's data distribution, and performing clustering for a remaining area of the color image that is not a part of the user-selected region of interest; and
applying hard thresholds to an adaptively-enhanced stain separation image to determine a nuclear area; and
performing nuclei number estimation for detecting abnormal cells including:
after receiving segmented patches, applying connected component analysis to analyze each local patch's shape;
voting on the center of each nuclear area, such that the higher a voting score, the more likely to be a real nuclear center;
filtering peaks caused by artifacts based on a local patch's shape; and
determining the number nuclei based on a number of voting peaks, wherein the number of nuclei is the same as the number of voting peaks; and
a processor coupled to the memory, the processor configured for processing the application.

16. The apparatus of claim 15 wherein the hard thresholds are user-specified values.

17. The apparatus of claim 15 wherein the hard thresholds are searched optimum values.

18. An apparatus comprising:
a non-transitory memory for storing an application, the application for:
performing nuclei area estimation comprising:
receiving a color image;
utilizing stain separation to separate two dominating color components, a first color corresponding to positive stains and a second color corresponding to negative stains;
utilizing a user-selected region of interest as training data; and
applying a Gaussian Mixture Model (GMM) to parameterize the user-selected region of interest's data distribution, and performing clustering for a remaining area of the color image that is not a part of the user-selected region of interest; and
performing nuclei number estimation for detecting abnormal cells, the nuclei number estimation comprising:
after receiving segmented patches, applying connected component analysis to analyze each local patch's shape; and
voting on the center of each nuclear area, such that the higher a voting score, the more likely to be a real nuclear center; and
a processor coupled to the memory, the processor configured for processing the application.

19. The apparatus of claim 18 wherein performing nuclei area estimation includes:
performing adaptive thresholding based on each color channel;
selecting a small region of interest for model training; and
applying hard thresholds to an adaptively-enhanced stain separation image to determine a nuclear area.

20. The apparatus of claim 18, wherein performing nuclei number estimation for detecting abnormal cells further includes:
filtering peaks caused by artifacts based on a local patch's shape; and
determining the number nuclei based on a number of voting peaks, wherein the number of nuclei is the same as the number of voting peaks.

* * * * *